United States Patent
MacDonald et al.

(10) Patent No.: US 6,210,396 B1
(45) Date of Patent: Apr. 3, 2001

(54) GUIDING CATHETER WITH TUNGSTEN LOADED BAND

(75) Inventors: Stuart R. MacDonald, Danvers; Zelda M. Anastos, Brighton; Albert H. Dunfee, Byfield, all of MA (US); Michael S. Noone, Londonderry, NH (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/339,499

(22) Filed: Jun. 24, 1999

(51) Int. Cl.⁷ .................................................. A61M 25/098
(52) U.S. Cl. ...................................... 604/529; 604/103.1
(58) Field of Search .................................. 604/529, 532, 604/523, 524, 526, 527, 20, 100.01, 103, 103.1, 264; 606/194

(56) References Cited

U.S. PATENT DOCUMENTS

| | | | |
|---|---|---|---|
| 4,464,176 | * 8/1984 | Wijayarathna | 604/164 |
| 4,469,483 | 9/1984 | Becker et al. | 604/280 |
| 4,577,637 | 3/1986 | Mueller, Jr. | 128/658 |
| 4,588,399 | 5/1986 | Nebergall et al. | 604/280 |
| 4,636,346 | 1/1987 | Gold et al. | 264/139 |
| 4,817,613 | * 4/1989 | Jaraczewski et al. | 128/658 |
| 4,898,591 | 2/1990 | Jang et al. | 604/282 |
| 4,981,470 | 1/1991 | Bombeck, IV | 128/635 |
| 5,045,072 | 9/1991 | Castillo et al. | 604/280 |
| 5,105,818 | * 4/1992 | Christian et al. | 128/662.06 |
| 5,147,315 | * 9/1992 | Weber | 604/164 |
| 5,171,232 | 12/1992 | Castiool et al. | 604/280 |
| 5,221,270 | 6/1993 | Parker | 604/282 |
| 5,234,416 | 8/1993 | Macaulay et al. | 604/282 |
| 5,250,034 | * 10/1993 | Appling et al. | 604/164 |
| 5,300,048 | 4/1994 | Drewes, Jr. et al. | 604/280 |

(List continued on next page.)

FOREIGN PATENT DOCUMENTS

| | | |
|---|---|---|
| 0 517 075 | 12/1992 | (EP) . |
| 1 004 327 A1 | 5/2000 | (EP) . |
| WO99/17829 | 4/1999 | (WO) . |

*Primary Examiner*—Sharon Kennedy
*Assistant Examiner*—Kevin C. Sirmons
(74) *Attorney, Agent, or Firm*—Sterne, Kessler, Goldstein & Fox P.L.L.C.

(57) ABSTRACT

The present invention comprises a tubular catheter shaft defining at least one catheter shaft lumen and a radiopaque band made of a polymeric material loaded with a radiopaque material of greater than 40% by weight, suitable for visualization under fluoroscopy in catheters in the range of 3 French to 5 French. The distal soft tip is formed of a relatively flexible polymeric material, loaded with radiopaque material which is less radiopaque than the radiopaque band. The radiopaque band's proximal end adjoins the distal end of the catheter shaft. The radiopaque band's distal end adjoins the proximal end of the distal tip to form an attachment junction. A tubular sleeve fits coaxially over the radiopaque band, the distal end of the catheter shaft and the proximal end of the distal soft tip. The tubular sleeve adheres the catheter shaft distal end to the proximal end of the radiopaque band and adheres the soft tip proximal end to the distal end of the radiopaque band thereby aligning the soft tip lumen, the radiopaque band lumen, and the catheter shaft lumen. The proximal end of the tubular sleeve is bonded to a distal portion of the catheter shaft. The distal end of the tubular sheath is bonded to the proximal end of the soft distal tip. The radiopaque band is bonded to the tubular sheath thereby bridging the attachment junction. The tubular sleeve is made of a polymeric material loaded with a radiopaque material which is less radiopaque than the radiopaque band. The tubular sleeve is melt compatible with the radiopaque band, the catheter shaft distal end and the distal soft tip such that the tubular sleeve, the distal end of the catheter shaft, the radiopaque band and the proximal end of the distal soft tip bond.

21 Claims, 5 Drawing Sheets

U.S. PATENT DOCUMENTS

| | | | |
|---|---|---|---|
| 5,403,292 | * 4/1995 | Ju | 604/282 |
| 5,429,597 | 7/1995 | DeMello et al. | 604/49 |
| 5,429,617 | 7/1995 | Hammersmark et al. | 604/264 |
| 5,456,251 | 10/1995 | Fiddian-Green | 128/632 |
| 5,456,705 | 10/1995 | Morris | 607/119 |
| 5,509,910 | 4/1996 | Lunn . | |
| 5,545,151 | * 8/1996 | O'Connor et al. | 604/282 |
| 5,560,120 | 11/1997 | Jacobsen et al. | 128/772 |
| 5,584,821 | 12/1996 | Hobbs et al. | 604/280 |
| 5,599,325 | * 2/1997 | Ju et al. | 604/282 |
| 5,603,991 | 2/1997 | Kupiecki et al. . | |
| 5,658,263 | * 8/1997 | Dang et al. | 604/280 |
| 5,725,513 | * 3/1998 | Ju et al. | 604/280 |
| 5,769,830 | 6/1998 | Parker | 604/282 |
| 5,853,400 | 12/1998 | Samson | 604/282 |
| 5,891,112 | * 4/1999 | Samson | 604/524 |

* cited by examiner

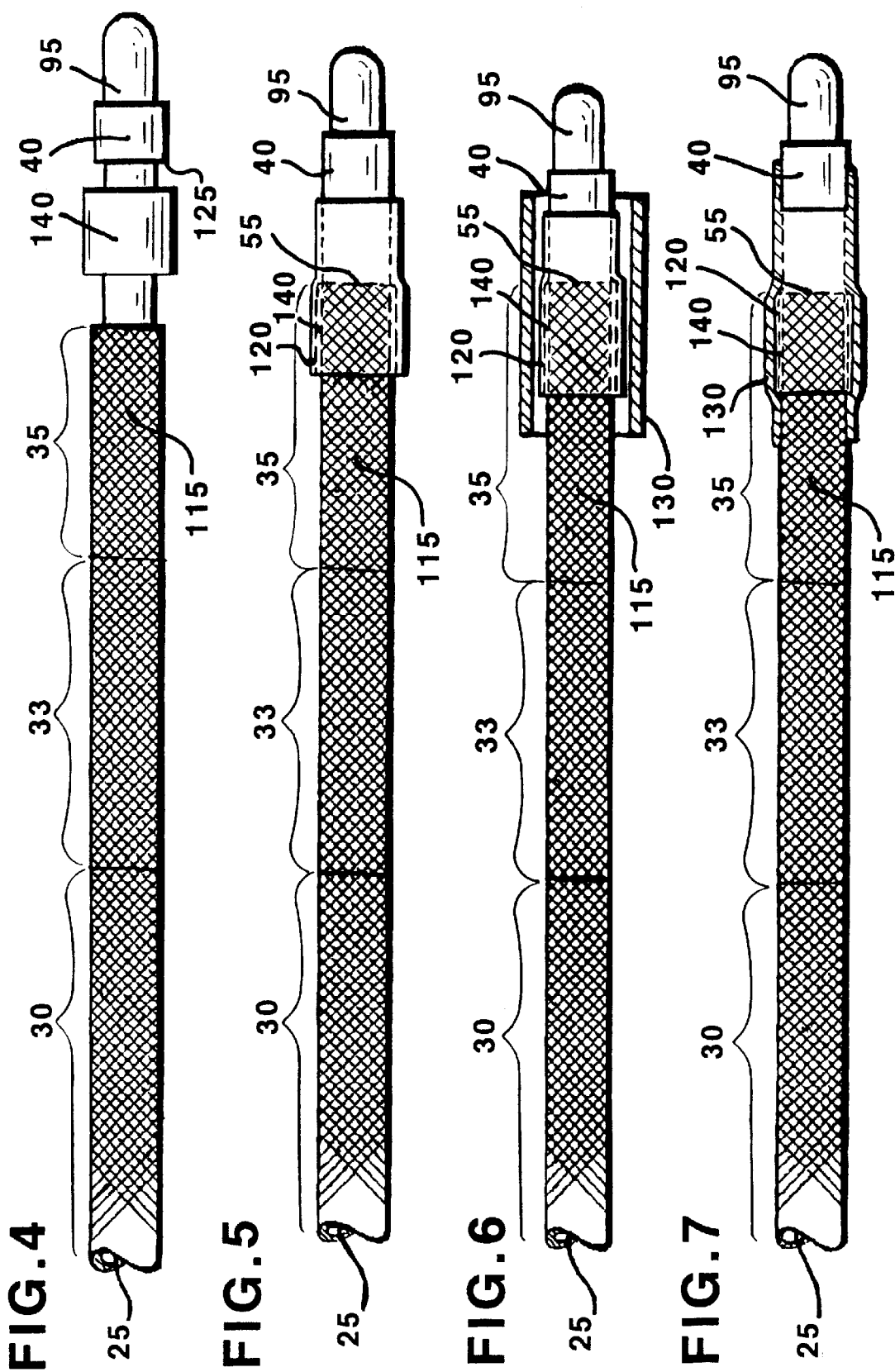

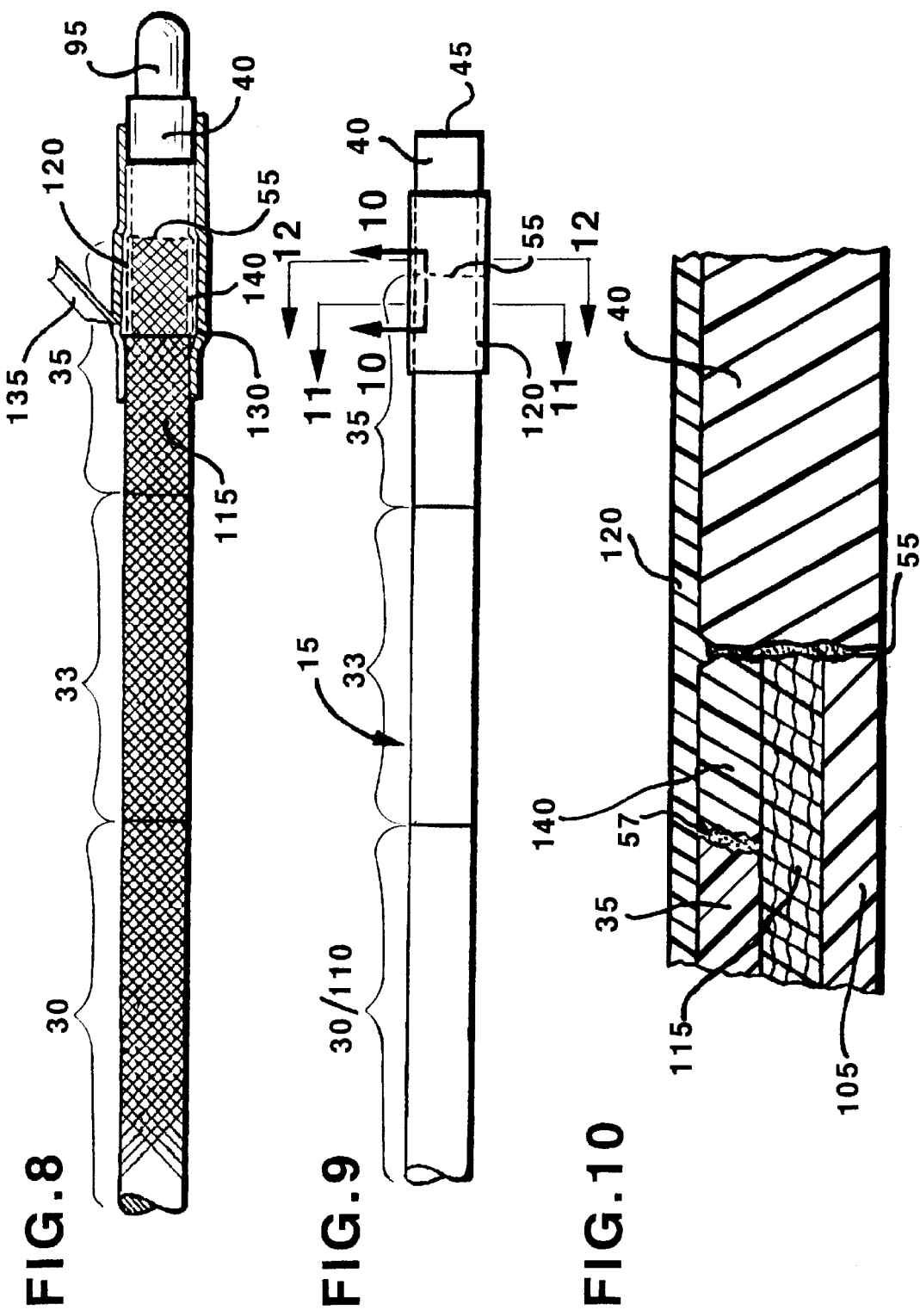

GUIDING CATHETER WITH TUNGSTEN LOADED BAND

CROSS-REFERENCE TO RELATED PENDING APPLICATIONS

Reference is made to commonly assigned U.S. Pat. No. 6,068,622 filed Feb. 10, 1998, for SINGLE PIECE HUB/STRAIN RELIEF THAT CAN BE INJECTION MOLDED OVER A SHAFT, in the names of Ghaleb A. Sater et al., U.S. patent application Ser. No. 09/046,241 filed Mar. 23, 1998, for CATHETER HAVING EXTRUDED RADIOPAQUE STRIPES EMBEDDED IN SOFT TIP AND METHOD OF FABRICATION, in the names of Nasser Rafiee et al. and U.S. patent application Ser. No. 09/188,760 filed Nov. 9, 1998 for GUIDING CATHETER AND METHOD OF FABRICATION, in the name of Thierry Benjamin.

FIELD OF THE INVENTION

The present invention relates to medical vascular catheters adapted to be inserted into a blood vessel from an incision through the skin of a patient for introducing other devices or fluids for diagnostic or therapeutic purposes, and particularly to a distal soft tip with a tungsten loaded band segment between the catheter shaft and the distal soft tip, the tungsten loaded band being more radiopaque than the distal soft tip.

BACKGROUND OF THE INVENTION

Catheters are tube-like medical instruments that are inserted into a body cavity organ or blood vessel for diagnostic or therapeutic reasons. Medical vascular catheters are particularly designed for insertion into the vasculature and are available for a wide variety of purposes, including diagnosis, interventional therapy, drug delivery, drainage, perfusion, and the like. Medical vascular catheters for each of these purposes can be introduced to numerous target sites within a patient's body by guiding the catheter through an incision made in the patient's skin and a blood vessel and then through the vascular system to the target site.

Medical vascular catheters generally comprise an elongated, flexible catheter tube or body with a catheter side wall enclosing a catheter lumen extending between a catheter body proximal end coupled to a relatively more rigid catheter hub to a catheter body distal end. The catheter body may be relatively straight, or may inherently curve, or may be curved by insertion of a curved stiffening wire or guide wire through the catheter lumen. The catheter body and catheter side wall are typically fabricated and dimensioned to minimize the catheter body outer diameter and side wall thickness, and to maximize the catheter lumen diameter while retaining sufficient side wall flexibility and strength characteristics to enable the catheter to be used for the intended medical purpose.

One of the therapeutic procedures applicable to the present invention is known as percutaneous transluminal coronary angioplasty ("PTCA"). PTCA can be used, for example, to reduce arterial build-up of cholesterol fats or atherosclerotic plaque. Catheters must have sufficient stiffness to be pushed through vessels as well as rigidity to provide a high degree of torsional control. Stiffness or rigidity in the catheter tip poses the danger of puncturing or otherwise damaging a vessel as it twists through the vascular system. It is therefore desirable for catheters to have a soft or flexible distal tip.

Commonly-owned U.S. patent application Ser. No. 09/188,760 filed Nov. 9, 1998 for GUIDING CATHETER AND METHOD OF FABRICATION, in the name of Thierry Benjamin describe various prior art methods of attaching distal soft tips to proximal catheter shafts and their improvements upon those methods.

U.S. patent application Ser. No. 09/046,241 filed Mar. 23, 1998, for CATHETER HAVING EXTRUDED RADIOPAQUE STRIPES EMBEDDED IN SOFT TIP AND METHOD OF FABRICATION, in the names of Nasser Rafiee et al. describes a catheter shaft having a radiopaque stripe(s) co-extruded in the side wall of the catheter shaft. In the co-extrusion process, one or more radiopaque stripes can be formed such that each extends substantially parallel with the axis of the tube and with one another. Alternatively, the shaft can be rotated as the co-extrusion takes place to form one or more spiral stripes of the radiopaque material. A disadvantage of the invention is that making the stripes wide enough to be seen under fluoroscopy makes the shaft stiffer and less flexible.

U.S. Pat. No. 5,045,072 to Castillo et al. for CATHETER HAVING HIGHLY RADIOPAQUE, FLEXIBLE TIP describes a distal tip of plastic formulation containing sufficient radiopaque agent (40–75% by weight) to be substantially more radiopaque and preferably softer than portions of the catheter proximal to the tip. Typically, transition zone 13 is free of tubular reinforcing braid, while catheter body 15 carries such reinforcing braid in its interior, in conventional manner. A disadvantage of the '072 invention is that adding metal to the distal soft tip makes it stiffer, thereby leading to greater trauma in the blood vessels. Another disadvantage of the '072 invention is that of not having a reinforcing braid in the transition zone, thereby compromising torkability and kink resistance.

U.S. Pat. No. 5,234,416 to Macaulay et al. for INTRAVASCULAR CATHETER WITH A NONTRAUMATIC DISTAL TIP describes a braided tubular member formed of a plurality of multifilament strands which are impregnated with a thermoset polymeric resin, the thermoset polymer resin which is incorporated into a distal portion of the braided tubular member. The distal tip has at least two relatively short, tubular elements, including a first (proximal) tubular element which is secured to the distal end of the catheter shaft and a second (distal) tubular element which is secured to the first (proximal) tubular element and which is softer than the first tubular element. The first (proximal) tubular element has a radiopaque filler material incorporated therein, such as bismuth trioxide, in order to make the distal tip fluoroscopicaly observable within a patient. The first and second tubular elements are but joined together by suitable means such as by heat fusing or by a suitable adhesive such as cyanoacrylate-based adhesive, e.g., Loctite® 405. A disadvantage of the Macaulay et al. guiding catheter is that the braided material terminates prior to the radiopaque area thereby compromising torkability and kink resistance.

Problems encountered in adding radiopaque material to a portion of a catheter include the stiffening of the area with the radiopaque material and the raising of the melt temperature of the area with the radiopaque material, thereby making the melt temperatures incompatible with the surrounding areas, thus making melt bonding to the adjoining areas difficult.

Visualizing the distal tip of a catheter under fluoroscopy is important for proper placement of the tip. The problem presented by stiffening due to radiopaque loading is that stiffening disproportionately increases as the walls of a catheter become thinner. In thin wall catheters therefor, less radiopaque material can be loaded than with catheters with thicker walls, thereby reducing visualization in thin wall catheters. For example, 35–40% by weight of $BaSO_4$ in a 5 French catheter would not be visible under fluoroscopy. Loading high enough amounts of such radiopaque material sufficient for the visualization of the distal tip, however, makes the distal tip too stiff.

It is an object of the invention to enable the physician to see the catheter distal area under fluoroscopy without compromising the flexibility of the distal soft tip. It is a further object of the invention to have an area which is visible under fluoroscopy yet permits torque transfer and remains kink resistant.

SUMMARY OF THE INVENTION

The present invention comprises a tubular catheter shaft defining at least one catheter shaft lumen and a radiopaque band made of a polymeric material loaded with a radiopaque material of greater than 40% by weight, suitable for visualization under fluoroscopy in catheters in the range of 3 French to 5 French. The distal soft tip is formed of a relatively flexible polymeric material, loaded with radiopaque material which is less radiopaque than the radiopaque band. The radiopaque band's proximal end adjoins the distal end of the catheter shaft. The radiopaque band's distal end adjoins the proximal end of the distal tip to form an attachment junction. A tubular sleeve fits coaxially over the radiopaque band, the distal end of the catheter shaft and the proximal end of the distal soft tip. The tubular sleeve adheres the catheter shaft distal end to the proximal end of the radiopaque band and adheres the soft tip proximal end to the distal end of the radiopaque band thereby aligning the soft tip lumen, the radiopaque band lumen, and the catheter shaft lumen. The proximal end of the tubular sleeve is bonded to a distal portion of the catheter shaft. The distal end of the tubular sheath is bonded to the proximal end of the soft distal tip. The radiopaque band is bonded to the tubular sheath thereby bridging the attachment junction. The tubular sleeve is made of a polymeric material loaded with a radiopaque material which is less radiopaque than the radiopaque band. The tubular sleeve is melt compatible with the radiopaque band, the catheter shaft distal end and the distal soft tip such that the tubular sleeve, the distal end of the catheter shaft, the radiopaque band and the proximal end of the distal soft tip bond.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the invention will become apparent from the following detailed description of the preferred embodiments of the invention, in which:

FIGS. 4 through 8 are plan views of the steps of a preferred method of attaching the distal soft tip and the tungsten loaded band to the catheter shaft distal end along the attachment junction as well as employing molding a sleeve of thermoplastic material over the attachment junction. Braided tube 115 is shown before shaft sections 30, 33 and 35 are affixed. The component numbers indicate where the shaft sections 30, 33 and 35 will be placed;

FIG. 9 is a plan view of the sleeve overlying the distal tip. Shaft sections 30/110, 33 and 35 have been affixed;

FIG. 10 is an enlarged cross-section view of the resulting catheter wall along the section lines 10—10 in FIG. 9;

DETAILED DESCRIPTION OF THE PREFERRED EMBODIMENTS OF THE INVENTION

The present invention provides an improved construction for catheters of the type having radiopaque distal ends. Applicant's radiopaque band 140 increases radiopacity in thin walled catheters. Applicant's tungsten loaded radiopaque band 140 offers a high degree of radiopacity near the distal tip of the catheter without adversely affecting the flexibility, torquability and kink resistance of the distal tip 40. Applicant's invention can be used with a variety of catheters, as for example, guiding catheters, diagnostic catheters, balloon catheters, sheaths and sleeves.

Figure 1:
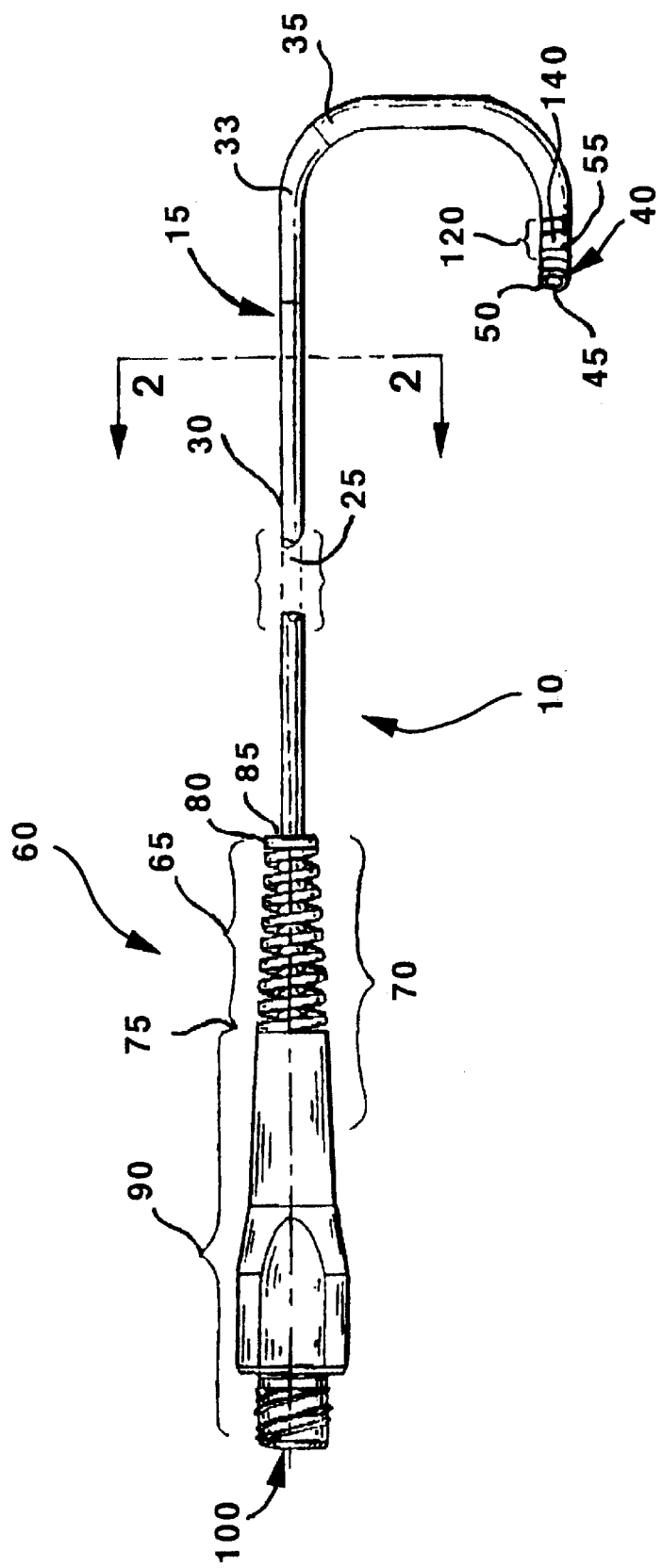
FIG. 1 is a plan view of an exemplary medical vascular catheter constructed with a the tip incorporating the tungsten loaded band and an overlying sleeve in accordance with a preferred embodiment of the invention.

In a broad overview of the present invention, the catheter body 15 comprises at least a catheter shaft, a radiopaque band 140 and a distal soft tip 40. The catheter shaft may be constructed in any acceptable manner to provide desired characteristics. FIG. 1 is intended to encompass any such construction and to illustrate the completed catheter 10 in accordance with the method of the present invention.

Refer to FIG. 1 which depicts an elongated catheter body and catheter hub 90 at the catheter body proximal end with at least one catheter lumen 100 extending through the catheter hub and body and to a catheter body distal end thereof. The catheter body 15 is formed of a catheter shaft 30 having a catheter shaft proximal end coupled to the catheter hub 70 and of a relatively short and tubular distal soft tip 40 coupled to the catheter shaft distal end. Such constructions are particularly useful for forming medical vascular catheters in a wide range of catheter body lengths and outer diameters. Such catheters include small diameter vascular catheters, having catheter body outside diameters of 4 mm (12 F.) preferably below 2.67 mm (8 F.), and frequently as small as 1 mm (3 F.), and below, such as those used in neurological diagnostic and interventional procedures. Such small diameter vascular catheters will also be useful for other procedures, such as gynecological procedures, cardiac procedures, general interventional radiology procedures, and the like, for access to the small vasculature as necessary. Constructions of the present invention, however, are not limited to such small diameter catheters, and will be useful for larger diameter catheters as well, such as vascular guiding catheters and PTA balloon catheters which may have outside diameters larger than 4 mm.

Medical vascular catheters according to the present invention will comprise a catheter body having dimensions, a particular side wall construction and a geometry selected for the intended use. The catheter body 15 will typically have a length in the range from about 40 cm to 200 cm, usually having a length in the range from about 60 cm to 175 cm. The outside diameter of the catheter body will typically be in the range from about 0.33 mm (1 F.) to 4 mm (12 F.), usually being in the range from about 0.66 mm (2 F.) to about 3.33 mm (10 F.). The catheter body will define an inner lumen 25 typically having a diameter in the range from about 0.1 mm to 3.6 mm, usually being in the range from about 0.3 mm to 3.0 mm, with catheters having larger outside diameters usually having larger catheter lumen diameters.

FIG. 1 is a plan view of an exemplary medical vascular catheter 10 constructed with a unitary catheter hub and strain relief 60 of the type disclosed in the above-referenced commonly owned '682 and '241 patent applications, for example. In this illustrated embodiment, the unitary catheter hub and strain relief 60 is injection molded as a single piece over a catheter hub/body junction 70 and includes a proximal hub portion 90 and a strain relief coil 65 made of a polymer such as Vestamid® available from Huls America Inc., Turner Place, Piscataway, N.J. 08855-0365. Vestamid® is a Polyamid 12. Those skilled in the art would recognize that any suitable hub and strain relief would be satisfactory. An example of a suitable hub and strain relief combination is depicted in FIG. 1 where the hub portion 90 surrounds and defines a hub lumen 100 extending to the catheter body lumen 25 of the catheter body 15. The proximal hub portion 90 is integrally connected to the proximal strain relief coil end 75 of the strain relief coil 65. The strain relief coil 65 is a continuous coil of constant or variable pitch having coil turns that decrease in diameter from the proximal strain relief coil end 75 to the distal strain relief coil end 80. The turns of the strain relief coil 65 are preferably molded over a distal portion of exterior surface of the catheter body 15 in the catheter hub/body junction 70 and adhered in a spiral pattern to the exterior surface of the catheter body. In this manner, a strain relief coil lumen 85 is effectively formed because the distal portion of exterior surface of the catheter body 15 extending the length of the catheter hub/body junction 70 functions as a mandrel. This construction is merely exemplary, and it will be understood that the present invention can also be implemented in a catheter employing a catheter hub of any of the known configurations.

The catheter body 15 will usually be straight along all or most of its length, that is, it will assume a straight or linear configuration, when free from external bending forces. The catheter body 15, however, will be highly flexible so that it will be able to pass through the tortuous twists and turns of a patient's vasculature. In some cases, the catheter body 15 may have a shaped distal end portion including curves and bends which are selected to facilitate introduction and placement of the catheter 10 (usually over a separate guide wire) in the vascular system. A particular geometry of curves and/or bends may be selected to accommodate the intended use of the catheter 10.

In FIG. 1, the catheter shaft 30 extends from the unitary catheter hub and strain relief 60 to a location spaced within 1 cm of the catheter body distal end 50. Usually catheter shaft 30 extends to a location spaced within 2 mm to 6 mm of the catheter body distal end 50 and preferably extends to location within about 3.5 mm of the catheter body distal end 50. The proximal catheter shaft 30 is preferably reinforced in catheter shaft side wall 20 as described below to have sufficient column strength and hoop strength for advancement through the incision in the patient's skin and blood vessel and through the tortuous vasculature. It will be understood that catheter shaft can be constructed in other ways than specifically described below to achieve this end. The construction, however, of the catheter shaft makes it relatively stiff and makes it possible to perforate a blood vessel wall if the catheter shaft distal end is aimed against it and advanced. The applicant's distal soft tip 40 that is attached to the catheter shaft distal end is intended to offset that possibility.

Figure 3:
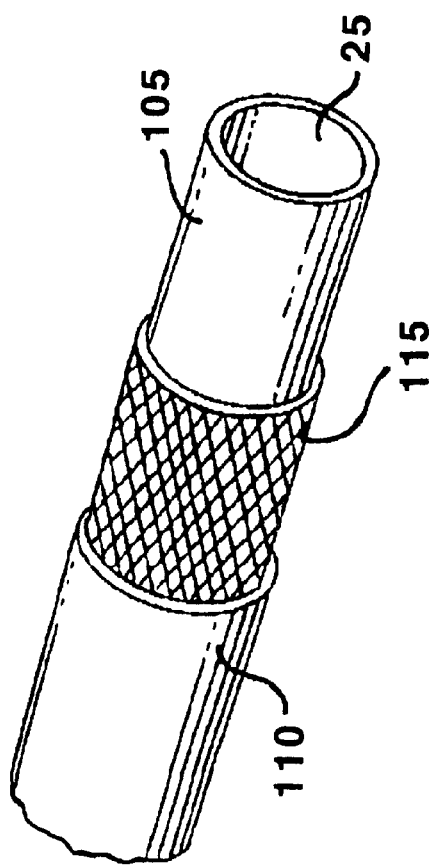
FIG. 3 is a perspective view of a section of the catheter shaft peeled back to reveal an inner tubular sheath, an outer tubular sheath and a wire braid tube sandwiched between the inner and outer tubular sheathes.
Figure 2:
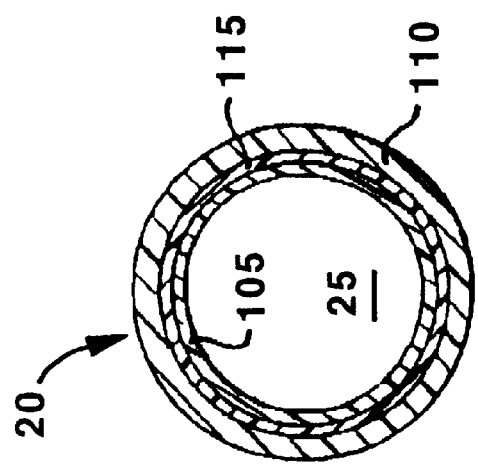
FIG. 2 is an enlarged cross-section view of the catheter shaft taken along lines 2—2 in FIG. 1.
Figure 12:
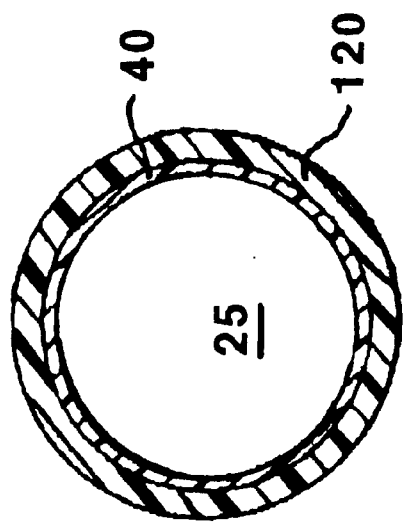
FIG. 12 is an enlarged cross-section view of the distal end of the catheter taken along lines 12—12 in FIG. 9.
Figure 11:
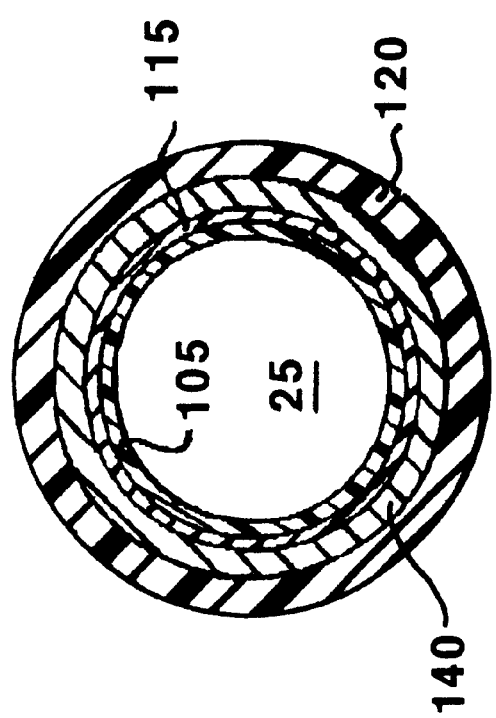
FIG. 11 is an enlarged cross-section view of the distal end of the catheter taken along lines 11—11 in FIG. 9.

A preferred embodiment of the construction of the catheter shaft side wall 20 of the catheter shaft 30 is depicted in FIGS. 2 and 3. The outer diameter of the catheter side wall 20 is approximately 0.0675 inches with an inner diameter of approximately 0.058 inches for a 5 French guiding catheter, for example. The invention, however, is applicable to a catheter of any conventional French size. The catheter shaft side wall 20 is preferably formed in the manner taught in the commonly assigned above-referenced '682 patent application. In accordance with this preferred embodiment of the invention, at least the proximal catheter shaft 30 is formed of an outer tubular sheath 110, an inner tubular sheath 105, and a wire braid tube 115 embedded in a polymer and sandwiched between the outer and inner tubular sheathes 110 and 105.

Typically, the inner tubular sheath 105 is formed from a single material suitable as a liner such as a lubricious polymer, as for example, a fluorocarbon (e.g., polytetrafluoroethylene (PTFE), a polyamide (e.g., nylon), polyether block amides (PEBA), a polyolefin, a polyimide, or the like. It would also be possible to form the inner tubular sheath 105 as a laminate structure comprising a non-lubricious outer layer and an inner lumen surrounding layer or coating of a more lubricious material. In one preferred embodiment, the inner sheath 105 is extruded of a polyether block-polyamide or a fluoropolymer such as TEFLON® from E.I. Du Pont de Nemours & Company, Wilmington, Del. The tubular sheath 105 liner has a side wall thickness of about 0.0254 mm to 0.08 mm in thin wall catheters such as 5 French, for example.

The wire braid tube 115 comprises "warp" and "weft" wire filaments braided in a fabric basket weave pattern wound to form a tube. The wire braid tube 115 may be woven directly over the inner tubular sheath 105 using conventional fabric weaving techniques. Or, the wire braid tube 115 may be woven over a mandrel using conventional braiding techniques and then fitted over the inner tubular sheath 105. The wire filaments have a very small cross-sectional area while possessing sufficient tensile strength to undergo the braiding process. Preferably, flat wire filaments of stainless steel, or a shape memory alloy (e.g., Nitinol), or polymeric fibers, or the like, are used. Stainless steel filaments having a flat cross-section with a thickness of 0.03 mm are particularly preferred for thin wall catheters such as 5 French, for example. A braid tube 115 with a cross-section thickness of less than 0.03 mm exhibits poor kink resistance and poor torqueability. Flat wire braid is preferable to round wire braid for thinwall catheters because it reduces wall thickness.

The catheter shaft is constructed of an outer tubular sheath 110 which is extruded or heat bonded over the wire braid tube 115 after the wire braid tube 115 is fitted or formed over the inner tubular sheath 105. The outer tubular sheath 110 can be formed of a variety of materials and is preferably composed of a thermoplastic material having a hardness in the range from Shore 30A to Shore 81D. Exemplary materials include polyamide or polyether block amides, polyurethanes, silicone rubbers, nylons, polyethylenes, fluorinated hydrocarbon polymers, and the like.

In the preferred embodiment seen in FIG. 1, the catheter shaft can be made in is multiple sections, as for example 3 sections which are serially disposed beginning at the proximal end with the proximal catheter shaft 30, the intermediate catheter shaft 33 and the distal catheter shaft 35. Those skilled in the art would recognize that a fewer number of sections or a greater number of sections would be acceptable. Each successive distal section should be more flexible than its immediately proximal section. The proximal catheter shaft 30 may comprise the outer tubular sheath 110 and may be made of a polyether-polyamide block copolymer. The intermediate catheter shaft 33 can also be made of a polyether-polyamide block copolymer, preferably with a hardness less than that of the proximal catheter shaft 30 and a hardness greater than that of the distal catheter shaft 35. The distal catheter shaft 35 can also be made of a polyether-polyamide block copolymer, preferably more flexible than the intermediate catheter shaft 33.

The radiopaque band 140 is serially disposed just distal to the distal catheter shaft 35 section and is coaxially disposed over the wire braid tube 115. Loading radiopaque material in the radiopaque band 140 just proximal to the distal tip 40 is preferred to loading radiopaque metals in the distal tip 40. Omitting or reducing the radiopaque metals in the distal tip 40 maintains the flexibility in the distal tip 40 while enabling the physician to closely approximate where the distal tip is located. Loading the radiopaque band 140 with greater than 40% radiopaque material by weight is required for successful visualization of thin wall catheters of between the sizes of 3 French and 5 French with the preferred loading being 80% by weight.

The radiopaque band 140 can be made of any polyether-polyamide block copolymer with a range between Shore 40D and 70D and more preferably a Vestamid® E62D-53 resin. The preferred radiopaque material for loading the radiopaque band 140 is tungsten at 80% by weight. The relatively high density of the tungsten (19.3 specific gravity) is particularly useful in thin walled guiding catheters such as those in the 3 French to 5 French range. The higher density of tungsten means that less of it will be required to achieve visualization. This is important where walls are thin. Those skilled in the art would recognize that other less dense radiopaque materials than tungsten would be acceptable such as $BaSO_4$, $BiSCO_3$, or $TiO_2$, although they would not appear as bright under fluoroscopy in is thin walled catheters such as 3 French to 5 French.

The radiopaque material is loaded into the polymer rather than using a metallic ring as in the prior art because the metallic ring is less flexible. It is also difficult to fuse a metallic ring to the adjoining sections of differing material properties such as differing melting temperature. The radiopaque band 140 is located immediately distal of the distal catheter shaft 35 distal end and is spaced within 30 cm of the catheter body distal end 50, usually from 1 cm to 10 cm of the catheter body distal end 50. The radiopaque band 140 is located immediately proximal of the distal soft tip 40. The distal soft tip 40 comprises the last 3 mm of the catheter. The radiopaque band 140 has a length in the range of 1.0 mm to 3.0 mm with a preferred length of about 1.5 mm. Any length which can be seen under fluoroscopy would be suitable. For 5 French catheters, for example, the radiopaque band 140 would have an inner diameter of about 0.069 inches, an outer diameter of about 0.073 inches and a wall thickness of about 0.002 inches. The inner diameter of the radiopaque band 140 should be sized to fit over the braid tube 115 and the inner tubular sheath 110 therein.

The radiopaque band 140 has an intermediate level of stiffness, column strength, and hoop strength between the relatively low levels of the distal catheter shaft 35 (made of Vestamid® E40-53, for example) and the relatively low levels of the distal soft tip 40 (made of PEBAX 40D loaded with $BaSO_4$ for example). The selection of the non-radiopaque materials for the radiopaque band 140, such as a polymer, is based upon considerations of tensile strength, processing temperature compatibility with the polymers comprising the distal catheter shaft 35 and distal soft tip 40, as well as considerations of the flexural modulus. The materials are selected to result in a minimum tensile strength necessary given the outer diameter and wall thickness of the catheter body.

When the radiopaque band 140 is fused to the metal braid tube 115, a radiopaque metal such as stainless steel, the radiopaque band 140 displays even better under fluoroscopy. The presence of the metal braid tube 115 in the radiopaque band 140 also imparts kink resistance and torqueability. Sections of differing materials which are joined are prone to kinking at the junction. Continuing the metal braid tube 115 into the radiopaque band 140 reduces kinking at junction 57.

Loading high amounts of radiopaque material in the radiopaque band 140, raises the melt temperature of that section, however, making the radiopaque band's 140 melt temperature incompatible with the adjoining sections of non radiopaque polymer materials. Thus it is difficult to melt bond a radiopaque loaded section with the adjoining non radiopaque materials. Loading materials which are compatible with the radiopaque band 140 into the adjoining tubular sleeve 120 and into the distal soft tip 40 solves this problem because the radiopaque band 140 becomes more melt compatible with both the distal soft tip 40 and the tubular sleeve 120, with the tubular sleeve 120 operating as a bridge to hold the assembly together. The polymer materials selected for the distal shaft 35, the radiopaque band 140, the distal tip 40 and the sleeve 120 should also be melt compatible to permit the successful bonding of these sections.

The tubular sleeve 120 is made of a polyether-polyamide block copolymer having a hardness in the range of Shore 40D to 70D loaded with a radiopaque material and more preferably. Vestamid® E62 which has been loaded with $BaSO_4$ at 35–40% by weight. $BaSO_4$ is faintly radiopaque and was chosen for its metallic properties which make it melt compatible with the tungsten loaded into radiopaque band 140 and with the $BaSO_4$ loaded into distal soft tip 40. The tubular sleeve 120 polymer is chosen for its bonding compatibility with the polymers in the distal catheter shaft 35, the distal soft tip 40 and the radiopaque band 140. Tubular sleeve 120 is approximately 6 cm long and extends over the entire radiopaque band 140, the proximal end of the distal tip 40 and the distal end of the catheter shaft distal end 35, the tubular sleeve 120 acting as a bridge to cause the radiopaque band 140, the distal soft tip 40 and the tubular sleeve 120 to achieve melt temperatures compatible enough to result in the heat bonding of these areas.

In the preferred embodiment, the distal shaft 35 of the catheter is affixed to the proximal end of the radiopaque band 140. The distal end of the radiopaque band 140 is affixed to the proximal end of the soft tip 40. The distal soft tip 40 is tubular and has a side wall that surrounds the soft tip lumen which is the distal part of the catheter body lumen 25 and terminates at the distal lumen end opening 45.

The distal soft tip 40 will generally be relatively short, typically having a length in the range from about 1.0 mm to 3.0 cm. Preferably, the distal soft tip 40 extends about 0.5 mm to 3.5 mm and preferably 2.0 mm distally from the distal end of the sleeve 120. The distal soft tip 40 extends proximally within the sleeve 120. The side wall of the distal soft tip 40 is flexible enough so that the side wall can buckle slightly when it bears against a blood vessel side wall and will not perforate the blood vessel side wall. The selection of polymer materials for the distal soft tip 40 in relation to the polymer materials of the catheter shaft outer tubular sheath 110 is also based upon considerations of flexural modulus and tensile strength.

The distal soft tip 40 is preferably pre-formed having an inner lumen, side wall thickness and outer diameter that is compatible with the dimensions of the catheter shaft 30, 33, 35 or any additional intermediate transition segments. In accordance with the above referenced '241 application, one or more radiopaque stripes can be co-extruded with the extrusion of the tubular side wall of the tubing from which the distal soft tip 40 is cut.

FIGS. 4–8 show the sequential attachment steps of the method of the present invention. FIG. 4 depicts the radiopaque band 140 and the distal soft tip 40 slipped over a mandrel 95 to be aligned with and attached to the distal catheter shaft 35. The stainless steel mandrel 95 is sized for a sliding fit within catheter shaft lumen 25 and to provide rigidity and maintain concentricity for subsequent bonding of components. Any conventional method of affixing the catheter sections can be used as for example, heat bonding, Radio Frequency bonding or adhesives.

To assemble, the extruded inner tubular sheath 105 is positioned with approximately 5.0 cm of the mandrel 95 extending distal to the catheter tubular sheath 105. Coaxially slide the wire braided tube 115 over the tubular sheath 105, or braid directly over the tubular sheath 105. Slide the intermediate shaft 33 over the wire braided tube 115 coaxially and overlap the proximal end of the intermediate shaft 33 with the distal end of the outer tubular sheath (proximal shaft 30) by approximately 1 mm. Slide the distal shaft 35 over the wire braided tube 115 coaxially and abut the distal end of the intermediate shaft with the proximal end of the distal shaft 35. Slide the radiopaque band 140 over the wire braided tube 115 coaxially and abut the distal end of the distal shaft 35 with the proximal end of the radiopaque band 140 such that the inner tubular sheath 105 and the braid tube 115 will extend under the radiopaque band 140. The distal ends of the radiopaque band 140, the inner tubular sheath 105 and the braid tube 115 will be co-terminus. Attach the intermediate catheter shaft 33, the distal catheter shaft 35 and the radiopaque band 140 using any conventional method of affixing catheter sections such as molding the assembly in a hot block using heat shrink tubing. Remove the excess wire braid 115 beyond the distal end of the radiopaque band 140 as the wire braid 115 should not extend into the distal tip 40 as it would cause excessive stiffening. Slide the distal tip 40 over the mandrel 95 coaxially and abut the distal ends of the radiopaque band 140, the inner tubular sheath, and the braid tube 115 with the proximal end of the distal tip 40. Attach the distal soft tip 40 to the radiopaque band using any conventional method of bonding such as RF energy, adhesives or heat bonding. Slide tubular sleeve 120 over the entire radiopaque band 140, the distal end of the distal shaft 35 and the proximal end of the distal soft tip 40 such that sleeve 120 extends beyond the proximal end of the radiopaque band 140 by approximately 0.75 mm as seen in FIG. 5 and covers the attachment junctions 55 and 57. Attach the sleeve 120 using any conventional method of affixing catheter sections including heat shrink tube 130 as seen in FIG.

6. Mold the assembly in a heated die hot block as seen in FIG. 7. Remove the heat shrink tube 130 as seen in FIG. 8. Attachment junction 55 occurs between the distal end of the radiopaque band 140 and the proximal end of the distal tip 40. Attachment junction 57 occurs between the distal end of the distal shaft 35 and the proximal end of the radiopaque band 140.

A sub-assembly of the catheter shaft 30, 33 and 35, the radiopaque band 140 and the distal soft tip 40 is formed as the materials of the abutting ends melt together. In this process, the reinforcing wire braid tube 115 just proximal to the junction 55 can become exposed due to melting and shrinkage of the catheter shaft outer tubular sheath 110. The radiopaque band 140 acts as a means to further cover the distal ends of the reinforcing wire braid tube 115.

The sleeve 120 preferably has an inner diameter of 0.069 inches and an outer diameter of 0.073 inches for a 5 French guiding catheter, for example. This results in a tube wall is thickness of 0.002 inches. The sleeve has a 3.0 mm length. The inner diameter of sleeve 120 is selected to be just sufficiently larger than the catheter body outer diameter to allow it to be slid over the distal soft tip 40, the radiopaque band 140 and the distal catheter shaft 35 to the position shown in FIG. 5.

After the sleeve 120 is positioned as shown in FIG. 5, a further heat shrink tube 130 (shown in cross-section in FIGS. 6–8) is fitted over the sleeve 120 as shown in FIG. 6. The heat shrink tube 130 extends proximally a distance of about 50 mm from the proximal end of the sleeve 120 and distally about 13.5 mm distal to the distal end of the sleeve 120 and may optionally extend over the mandrel 95. The assembly of FIG. 6 is then subjected to heat to effect the shrinkage of the heat shrink tube 130 tightly against the sleeve 120 and portions of the distal soft tip 40 and the catheter shaft 30 as shown in FIG. 7. The heat continues to be applied for a sufficient time to cause the sleeve 120, the underlying radiopaque band 140, distal soft tip 40, wire braid tube 115, the distal catheter shaft 35, and inner lining tubular sheath 105 to partially melt and bond. The heat shrink tube 130 is preferably formed of Teflon FEP (fluorinated ethylene propylene) which does not melt and mix with these catheter body and sleeve materials. The shrinkage of the heat shrink tube 130 applies compressive force to the thin walled sleeve 120 and forces it against the adjoining surfaces. The sleeve 120 is compressed from its starting wall thickness of about 0.76 mm to a resulting thin film thickness of about 0.38 mm which only slightly increases the outer diameter of the catheter body.

In FIG. 8, the heat shrink tube 130 is cut using a blade 135 along its length taking care to avoid cutting the underlying sleeve 120 revealing the resulting catheter body 15 shown in FIG. 9. In FIG. 9, the thickness of sleeve 120 is exaggerated from what is actually realized using this process with the materials and sleeve wall thickness described above. In practice, the tubular sleeve has an outer diameter that is 2.108 mm to 2.159 mm greater than the catheter shaft and the distal soft tip outer diameters. The thickness of sleeve 120 is barely perceptible to touch or sight, and the presence of the sleeve 120 can only be observed because it is tinted to have a different color for identification than the colors of the distal catheter shaft 35, the radiopaque band 140 and the distal soft tip 40.

The composite catheter body wall at the attachment junctions 55 and 57 are shown in FIG. 10. The melt zone formed along the attachment junctions 55 and 57 fills any interstitial spaces caused by the irregular points of mutual contact of the radiopaque band 140.

When an intermediate or transition segment is employed between the distal end of the distal catheter shaft 35 and the proximal end of the radiopaque band 140, the sleeve 120 may be elongated to extend over the additional segment(s) and over a distal portion of the distal catheter shaft 35 and a proximal portion of the distal soft tip as described above with respect to the preferred embodiment. Alternatively, an additional separate sleeve like sleeve 120 can be positioned to bridge the additional attachment junction(s) of the abutting distal and proximal ends of the catheter shaft 30, 33 and 35 and the transition segment. The same technique can be followed for any number of intermediate segments. In all such cases, the method steps of FIGS. 4–8 are followed to minimize the thickness of the sleeve 120 and provide strong adhesion between it and the underlying catheter shaft portion and segment portion outer walls adjoining each attachment junction.

In all such cases, a strong bond can be formed at each abutting attachment junction if the polymer materials of the distal catheter shaft 35, any intermediate segment(s), the radiopaque band 140 and the distal soft tip are chosen to have melt compatibility within a common temperature range. The above specified VESTAMID and PEBAX® polyether-polyamide block copolymer tube materials having the differing Shore hardnesses have compatible melt temperatures and adhere well to one another.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

PART LIST FOR FIGS. 1–10 medical vascular catheter 10
catheter body 15
catheter shaft side wall 20
catheter body lumen 25
proximal catheter shaft 30
intermediate catheter shaft 33
distal catheter shaft 35
distal soft tip 40
distal lumen end opening 45
catheter body distal end 50
attachment junction 55 to distal tip
attachment junction 57 to distal shaft
unitary catheter hub and strain relief 60
strain relief coil 65
catheter hub/body junction 70
proximal strain relief coil end 75
distal strain relief coil end 80
strain relief coil lumen 85
proximal hub portion 90
mandrel 95
hub lumen 100
inner tubular sheath 105
outer tubular sheath 110
braid tube 115
tubular sleeve 120
soft tip proximal end 125
heat shrink tube 130
blade 135
Radiopaque Band 140

What is claimed is:

1. A catheter body comprising:

a proximal, tubular catheter shaft, the catheter shaft formed of a relatively stiff polymeric material extending between a catheter shaft proximal end and a catheter shaft distal end, the catheter shaft having a catheter shaft outer diameter and defining at least one catheter shaft lumen extending between the catheter shaft proximal and distal ends;

a radiopaque band made of polymeric material loaded with a radiopaque material of greater than 40% by weight, the radiopaque band having an inner diameter, an outer diameter, a distal end, a proximal end, and defining at least one lumen, the radiopaque band;

a distal soft tip formed of a relatively flexible polymeric material, loaded with radiopaque material which is less radiopaque than the radiopaque band, the distal soft tip extending between a soft tip proximal end and a soft tip distal end, the distal soft tip having a soft tip outer diameter and at least one soft tip lumen extending between the soft tip proximal end and the soft tip distal end, the radiopaque band proximal end adjoining the catheter shaft distal end and the radiopaque band distal end adjoining the distal soft tip proximal end to form attachment junctions; and a tubular sleeve defining a tubular sleeve lumen, the tubular sleeve fitting coaxially over the radiopaque band, the catheter shaft distal end and the distal soft tip proximal end, the tubular sleeve adhering the catheter shaft distal end to the proximal end of the radiopaque band and the tubular sleeve adhering to the soft tip proximal end to the distal end of the radiopaque band thereby aligning the soft tip lumen, the radiopaque band lumen, and the catheter shaft lumen, the proximal end of the tubular sleeve being bonded to a distal portion of the catheter shaft, the distal end of the tubular sleeve being bonded to the proximal end of the soft distal tip, the radiopaque band being bonded to the tubular sleeve thereby bridging the attachment junctions, wherein the tubular sleeve is melt compatible with the radiopaque band, the catheter shaft distal end and the distal soft tip such that the tubular sleeve, the catheter shaft distal end, the radiopaque band and the distal soft tip proximal end bond.

2. The catheter of claim 1, wherein the radiopaque band is made of a polyether-polyamide block copolymer in the range of 40D to 70D.

3. The catheter of claim 2, wherein the radiopaque band radiopaque material is tungsten.

4. The catheter of claim 3, wherein the tungsten loading is 80% by weight.

5. The catheter of claim 4, wherein the catheter shaft is at least partially comprised of a polyether-polyamide block copolymer thermoplastic material having a hardness of between Shore 30D and 81D.

6. The catheter of claim 5, wherein the distal soft tip is comprised of a polyether-polyamide block copolymer having a Shore durometer of about 40D–55D.

7. The catheter of claim 6, wherein the sleeve is comprised of a polyether-polyamide block copolymer having a Shore durometer of about 40D–70D.

8. The catheter of claim 1 wherein at least a portion of the shaft is made of an outer tubular sheath and an inner tubular sheath, the outer tubular sheath having a proximal end and a distal end, the outer tubular sheath defining an outer tubular sheath lumen, the outer tubular sheath lumen having the inner tubular sheath running longitudinally therethrough, the inner tubular sheath having a proximal end and a distal end, the inner tubular sheath defining an inner tubular sheath lumen.

9. The catheter of claim 8 wherein the inner tubular sheath is comprised of a lubricious polymer.

10. The catheter of claim 8 wherein the distal end of the outer tubular sheath abuts a proximal end of an intermediate section of lower hardness.

11. The catheter of claim 8 wherein the distal end of the inner tubular sheath abuts the proximal end of the distal soft tip.

12. The catheter of claim 8 having a braided tube having a proximal end and a distal end, the braided tube defining a braided tube lumen, the inner tubular sheath running longitudinally through the braided tube lumen, the braided tube running longitudinally through the outer tubular sheath, the distal end of the braided tube abutting the proximal end of the distal soft tip.

13. The catheter of claim 12 wherein the braided tube is made of flat wire filaments.

14. The catheter of claim 1 having a size ranging from 3 French to 5 French.

15. The catheter of claim 1, wherein the soft tip outer diameter and the catheter shaft outer diameter are substantially the same as the catheter shaft outer diameter.

16. The catheter of claim 1, wherein said tubular sleeve aligns the distal soft tip outer diameter, the radiopaque band outer diameter, and the catheter shaft outer diameter.

17. The catheter of claim 1, wherein said tubular sleeve is made of a polymeric material loaded with a radiopaque material which is less radiopaque than the radiopaque band.

18. The catheter of claim 17, wherein the tubular sleeve is made of a polyether-polyamide block copolymer in the range of Shore 40D to 70D.

19. The catheter of claim 1, wherein said distal soft tip is loaded with radiopaque material which is less radiopaque than the radiopaque band.

20. A catheter body comprising:
a proximal, tubular catheter shaft, the catheter shaft extending between a catheter shaft proximal end and a catheter shaft distal end;
a radiopaque band made of polymeric material loaded with a radiopaque material, the radiopaque band having a distal end, a proximal end, and defining at least one lumen;
a distal soft tip loaded with radiopaque material which is less radiopaque than the radiopaque band, the distal soft tip extending between a soft tip proximal end and a soft tip distal end, the radiopaque band proximal end adjoining the catheter shaft distal end and the radiopaque band distal end adjoining the soft tip proximal end to form attachment junctions; and
a tubular sleeve fitting coaxially over the catheter shaft distal end and the radiopaque band proximal end, wherein the tubular sleeve bonds with the catheter shaft distal end and the radiopaque band proximal end, bridging the attachment junction therebetween, wherein the tubular sleeve is melt compatible with the catheter shaft and the radiopaque band.

21. A catheter body comprising:
a proximal, tubular catheter shaft, the catheter shaft extending between a catheter shaft proximal end and a catheter shaft distal end;
a radiopaque band made of polymeric material loaded with a radiopaque material, the radiopaque band, a distal end, a proximal end, and defining at least one lumen;
a distal soft tip loaded with radiopaque material which is less radiopaque than the radiopaque band, the soft tip extending between a soft tip proximal end and a soft tip distal end, the radiopaque band proximal end adjoining the catheter shaft distal end and the radiopaque band distal end adjoining the soft tip proximal end to form attachment junctions; and
a tubular sleeve fitting coaxially over the radiopaque band distal end and the soft tip proximal end, wherein the tubular sleeve bonds with the radiopaque band distal end and the soft tip proximal end, bridging the attachment junction therebetween, wherein the tubular sleeve is melt compatible with the radiopaque band and the soft tip.

* * * * *

UNITED STATES PATENT AND TRADEMARK OFFICE
CERTIFICATE OF CORRECTION

PATENT NO.    : 6,210,396 B1  
DATED         : April 3, 2001  
INVENTOR(S)   : MacDonald et al.

Page 1 of 1

It is certified that error appears in the above-identified patent and that said Letters Patent is hereby corrected as shown below:

<u>Title page, Item [54] and Column 1, lines 1-2,</u>  
Delete "TUNGSTEN LOADED" and insert -- RADIOPAQUE -- therefor.

<u>Column 7,</u>  
Line 37, delete "E62D-53" and insert -- E62D-S2 -- therefor.

<u>Column 8,</u>  
Line 6, delete "E62D-53" and insert -- E62D-S2 -- therefor.

Signed and Sealed this

Tenth Day of June, 2003

JAMES E. ROGAN  
*Director of the United States Patent and Trademark Office*